US009620860B2

(12) United States Patent
Asplund et al.

(10) Patent No.: US 9,620,860 B2
(45) Date of Patent: Apr. 11, 2017

(54) SLOTTED WAVE GUIDE ANTENNA WITH ANGLED SUBSECTION

(75) Inventors: Henrik Asplund, Stockholm (SE); Jonas Medbo, Uppsala (SE)

(73) Assignee: TELEFONAKTIEBOLAGET LM ERICSSON (PUBL), Stockholm (SE)

( * ) Notice: Subject to any disclaimer, the term of this patent is extended or adjusted under 35 U.S.C. 154(b) by 111 days.

(21) Appl. No.: 14/001,715

(22) PCT Filed: Feb. 28, 2011

(86) PCT No.: PCT/EP2011/052942
§ 371 (c)(1),
(2), (4) Date: Aug. 27, 2013

(87) PCT Pub. No.: WO2012/116728
PCT Pub. Date: Sep. 7, 2012

(65) Prior Publication Data
US 2013/0335283 A1 Dec. 19, 2013

(51) Int. Cl.
*H01Q 13/10* (2006.01)
*H01Q 13/22* (2006.01)
(Continued)

(52) U.S. Cl.
CPC ............ *H01Q 13/22* (2013.01); *H01Q 13/16* (2013.01); *H01Q 13/20* (2013.01);
(Continued)

(58) Field of Classification Search
CPC ...... H01Q 13/00; H01Q 13/203; H01Q 13/22; H01Q 13/28; H01Q 19/15
(Continued)

(56) References Cited

U.S. PATENT DOCUMENTS 3,039,098 A 6/1962 Bickmore
3,963,999 A * 6/1976 Nakajima ............ H04B 5/0018 333/237
(Continued)

FOREIGN PATENT DOCUMENTS

CN 1557106 A 12/2004
JP 2005192036 A 7/2005
(Continued)

OTHER PUBLICATIONS

Office Action issued on Jul. 2, 2014 in corresponding Japanese Application No. 201180068646.8, 12 pages (English translation only).
(Continued)

*Primary Examiner* — Graham Smith
*Assistant Examiner* — Collin Dawkins
(74) *Attorney, Agent, or Firm* — Rothwell, Figg, Ernst & Manbeck, P.C.

(57) ABSTRACT

An antenna arrangement 30 comprising a leaky cable 31 is disclosed. The leaky cable 31 includes subsections 32, 33, 34 and each subsection exhibits a longitudinal direction of extension $L_{32}$, $L_{33}$, $L_{34}$ and a radiation pattern. The longitudinal directions of adjacent subsections are oriented in different directions to create a predetermined radiation pattern by superpositioning of the radiation pattern of each subsection. Additionally, a method of creating a predetermined radiation pattern of such an antenna arrangement 30 is described.

27 Claims, 5 Drawing Sheets

(51) Int. Cl.

| | |
|---|---|
| ***H01Q 13/16*** | (2006.01) |
| ***H01Q 13/20*** | (2006.01) |
| ***H01Q 21/00*** | (2006.01) |
| ***H01Q 21/29*** | (2006.01) |

(52) U.S. Cl.
CPC ......... *H01Q 13/203* (2013.01); *H01Q 13/206* (2013.01); *H01Q 21/005* (2013.01); *H01Q 21/29* (2013.01)

(58) Field of Classification Search
USPC .......................................... 343/767, 771, 772
See application file for complete search history.

(56) References Cited

U.S. PATENT DOCUMENTS

| | | | | |
|---|---|---|---|---|
| 4,084,141 | A * | 4/1978 | Miyamoto | H01Q 13/203 333/237 |
| 4,112,431 | A | 9/1978 | Wild | |
| 6,292,072 | B1 * | 9/2001 | Bode | H01Q 13/203 333/237 |
| 2004/0185910 | A1 * | 9/2004 | Matsushita | H01Q 13/203 455/562.1 |
| 2008/0049858 | A1 | 2/2008 | Matsushita | |
| 2008/0094296 | A1 | 4/2008 | Lee | |
| 2010/0217252 | A1 * | 8/2010 | Rossetto | A61B 18/1815 606/33 |

FOREIGN PATENT DOCUMENTS

| | | | |
|---|---|---|---|
| JP | 2006165779 | A | 6/2006 |
| JP | 2007295396 | A | 11/2007 |
| JP | 4227589 | B2 | 2/2009 |

OTHER PUBLICATIONS

Office Action issued by the State Intellectual Property Office of China in corresponding application No. 201180068646.8 on Mar. 25, 2015, 12 pages.

Office Action issued by the Mexican Intellectual Property Office in corresponding application No. MX/a/2013/009951 on Feb. 11, 2015, 12 pages.

Third Office Action issued by the State Intellectual Property Office of China in corresponding application No. 201180068646.8 on Sep. 18, 2015, 8 pages.

Communication issued in EP Application No. 11 705 000.5, dated Feb. 20, 2017, 8 pages.

Gomez-Tornero, "Analysis and Design of Control Tapered Leaky-Wave Antennas", IEEE Antennas and Wireless Propagation Letters, vol. 10, Jan. 1, 2011, 4 pages.

* cited by examiner

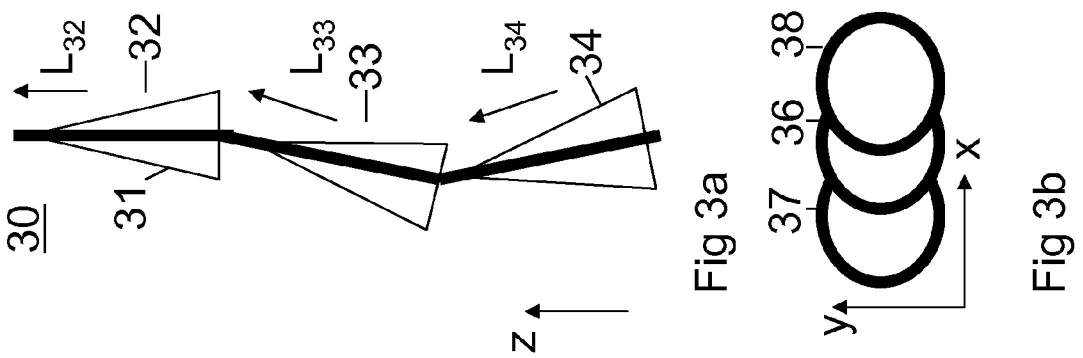
Fig 3a
Fig 3b
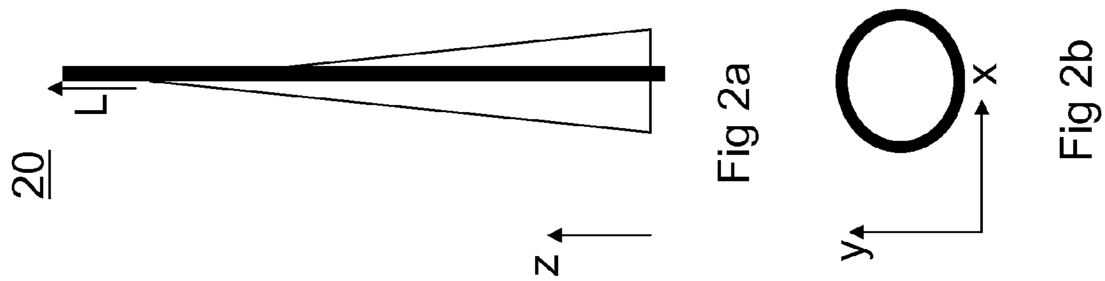
Fig 2a
Fig 2b

SLOTTED WAVE GUIDE ANTENNA WITH ANGLED SUBSECTION

CROSS-REFERENCE TO RELATED APPLICATION

This application is a 35 U.S.C. §371 National Phase Entry Application from PCT/EP2011/052942, filed Feb. 28, 2011, and designating the United States.

TECHNICAL FIELD

The present invention discloses a novel antenna arrangement and a method of creating a predetermined radiation pattern of the antenna arrangement.

BACKGROUND

When deploying wireless communications systems such as, for example, cellular systems, in indoor environments in general, so called "leaky cables" are sometimes used, also sometimes referred to as leaky feeders or radiating cables.

A leaky cable is a cable which is capable of conducting electromagnetic radio frequency energy, and which has been provided with apertures in order to make the cable radiate, i.e. to allow some of the energy to "leak" from the cable, thus enabling the cable act as an antenna. Such an antenna, i.e. a leaky cable, will due to reciprocity be able to act equally well as a receiving as a transmitting antenna. Due to its nature of a cable, a "leaky cable antenna" will, as compared to a traditional antenna, act more like a line source than a point source, obtaining a more uniform coverage level compared to a point source antenna from which the radiated power falls off rapidly with distance, thus making it easier to obtain coverage in tunnels, along railways or where a high degree of "shadowing" occurs when using a point source antenna. An example of the latter is an indoor scenario, e.g. an office landscape.

A leaky feeder is typically designed as a coaxial cable or a waveguide where the outer conductor is perforated in order to create holes or slots through which some of the energy in the cable can escape and radiate into free space. Various designs exist for the slot geometry and separations. The slots can be uniformly distributed along the length of the cable or clustered in groups, thereby providing different radiating properties. Variations of the slot structure, shape, and density along the cable allow a cable designer to shape how much the cable is radiating from different sections and also in what directions. The latter property is realized through selecting on which side of the cable the slots are placed, as each slot will have directional radiation properties that essentially form a lobe or beam away from the cable.

It has been found through measurements and numerical simulations that a leaky feeder will have its radial radiation maximum in the direction that the slots are facing. More importantly, depending on the frequency and slot separation, the maximum radiation will be in a cone at a certain polar angle from the longitudinal axis. When the radiation has its maximum along the cable it is said to operate in the coupling mode, while when the maximum is more perpendicular to the cable it is said to operate in the radiating mode. FIG. 1*a* illustrates the cone angle of radiation from a leaky cable in coupling mode and FIG. 1*b* illustrates the cone angle of radiation from a leaky cable in radiating mode.

While the leaky cable is well suited to achieve good coverage in the vicinity of the cable such as in indoor or underground deployments, it can be difficult to use it to provide coverage over wider areas due to the very high directivity that the cable has in the far field. A conical beam may also not be well suited to the coverage area. Prior art antennas which are more point source-like are preferably used in such scenarios, even though these antennas have limited degrees of freedom in shaping the radiation pattern due to the compact size. Regular antennas also rely on good impedance and radiation resistance matching in order to be effective radiators. Thereby they become sensitive to detuning due to e.g. objects or persons in the near field or in contact with the antenna.

SUMMARY

It is therefore an object of the present invention to address some of the problems and disadvantages outlined above and to provide an antenna arrangement with several degrees of freedom in shaping the radiation pattern of the antenna arrangement and a method of creating the radiation pattern of the antenna arrangement.

The above stated object is achieved by means of an antenna arrangement and a method for creating a radiation pattern of the antenna arrangement according to the independent claims, and by the embodiments according to the dependent claims.

In accordance with one embodiment, an antenna arrangement comprising an elongated structure for guiding an electromagnetic wave is provided. The elongated structure comprises subsections and radiation elements, wherein the radiation elements are through-going perforations in the elongated structure. Each perforation is adapted to allow a fraction of the total energy in the guided electromagnetic wave to be radiated out from the perforation. Furthermore, each subsection exhibits a longitudinal direction of extension and a radiation pattern. Moreover, the longitudinal directions of adjacent subsections are oriented in different directions to create a predetermined radiation pattern by superpositioning of the radiation pattern of each subsection.

In accordance with another embodiment, a method of creating a predetermined radiation pattern of an antenna arrangement is provided. The antenna arrangement comprises an elongated structure for guiding an electromagnetic wave. The elongated structure comprises subsections and radiation elements, wherein the radiation elements are through-going perforations in the elongated structure. Each perforation is adapted to allow a fraction of the total energy in the guided electromagnetic wave to be radiated out from the perforation. Furthermore, each subsection exhibits a longitudinal direction of extension and a radiation pattern. Moreover, the method comprises superpositioning the radiation pattern of each subsection and orienting the longitudinal directions of adjacent subsections in different directions to create the predetermined radiation pattern.

An advantage of particular embodiments is that they provide the additional degrees of freedom in synthesizing a suitable radiation pattern compared to prior art antenna designs. This can be utilized to create higher and/or more uniform antenna gain within an intended coverage area, while minimizing the antenna gain outside the same area which will lead to reduced interference towards and from neighbouring cells or services.

Another advantage of particular embodiments is that the antenna arrangement can easily be made to conform to an existing structure, such as the framework/truss of a tower, a slanted building roof or even the chassis of a phone or laptop. This may be utilized to reduce the visual impact and in some cases the wind load compared to prior art antennas e.g. panel antennas which are commonly used in current cellular networks.

Yet another advantage of particular embodiments is the low radiated power per unit length and corresponding low field strengths near the antenna arrangement. Comparing a 16 m meandering leaky cable antenna with a 1 m long prior art antenna design, both radiating the same power, it is evident that the electric field strength near the antenna will be reduced by a factor ¼. This is very beneficial for achieving compliance with regulatory safety limits for radio frequency exposure, which can in particular be limiting for small devices such as mobile phones or laptops.

Still another advantage of particular embodiments is that the eventual absorption of energy and thereby loss of energy due to the presence of e.g. a human user near or in contact with a hand-held device or a laptop will be much lower.

Yet another advantage of particular embodiments is the fact that each slot is a rather poor radiator, or in other words, that it has a rather poor impedance match to the intrinsic impedance of the elongated structure i.e. the leaky cable (usually 50 ohm). The benefit of this is that the presence of an object or a user very near a part of the cable only has a very limited detuning effect, in contrast the rather strong detuning that can be the result with a prior art antenna. Thus, the radiation efficiency of particular embodiments is quite insensitive to disturbances from objects in the near field.

Further advantages and features of embodiments of the present invention will become apparent when reading the following detailed description in conjunction with the drawings.

BRIEF DESCRIPTION OF THE DRAWINGS

For a better understanding, reference is made to the following drawings and preferred embodiments of the invention.

FIG. 2*a* shows a substantially straight leaky cable and the projection of the corresponding radiation pattern in the x-y-plane is illustrated in FIG. 2*b*.

FIG. 3*a* shows an antenna arrangement according to an exemplary embodiment and the projection of the corresponding radiation pattern in the x-y-plane is illustrated in FIG. 3*b*.

DETAILED DESCRIPTION

Figure 1A:
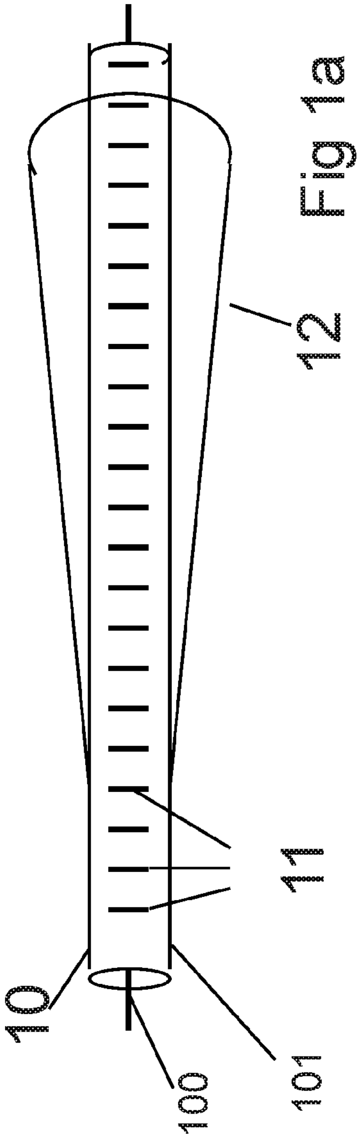
FIGS. 1*a* and 1*b* illustrate the cone angle of radiation from a leaky cable in coupling mode and the cone angle of radiation from a leaky cable in radiating mode, respectively.

In the following description, for purposes of explanation and not limitation, specific details are set forth, such as particular sequences of steps and particular device configurations in order to provide a thorough understanding of the present invention. It will be apparent to one skilled in the art that the present invention may be practised in other embodiments that depart from these specific details. In the drawings, like reference signs refer to like elements.

Moreover, those skilled in the art will appreciate that the means and functions explained herein below may be implemented using software functioning in conjunction with a programmed microprocessor or general purpose computer, and/or using an application specific integrated circuit (ASIC). It will also be appreciated that while the current invention is primarily described in the form of methods and devices, the invention may also be embodied in a computer program product as well as a system comprising a computer processor and a memory coupled to the processor, wherein the memory is encoded with one or more programs that may perform the functions disclosed herein.

The invention will be described below with reference to the accompanying drawings, in which the structures for guiding an electromagnetic wave are shown as coaxial cables (see e.g., FIG. 1*a*, which shows the inner conductor 100 and outer conductor 101 of a coaxial cable 10). It should however be pointed out that this is merely an example intended to enhance the reader's understanding of the invention and should not be seen as limiting the choice of structure, which can, for example, also comprise one or more of the following: waveguides, strip line arrangements, and micro strip arrangements.

The operation of an elongated structure, such as a leaky cable, as an antenna arrangement can mathematically be described as follows. A total of a number, N, radiating slots are positioned along the cable, with coordinates $\bar{r}_n = x_n\hat{x}+y_n\hat{y}+z_n\hat{z}$. The complex excitation $a_n$ of each slot is a function of the electric and magnetic field inside the elongated structure at the position of the slot, as well as the properties of the slot itself. Assuming that each slot is an isotropic radiator, the magnitude of the electric field at an observation point $\bar{r}'=x'\hat{x}+y'\hat{y}+z'\hat{z}$ can be expressed as the superposition of the complex field contribution from each slot as $$E(r') \propto \sum_{n=1}^{N} \frac{a_n e^{ik|\bar{r}_n - \bar{r}'|}}{|\bar{r}_n - \bar{r}'|^2}$$

where $k=2\pi/\lambda$ is the wave number.

The directive characteristics of each slot may of course be taken into account by making $a_n = a_n(\bar{r}_n - \bar{r}')$; even though the size of each slot in relation to the frequency is small, it provides the opportunity of optimizing the radiation pattern.

Figure 1B:
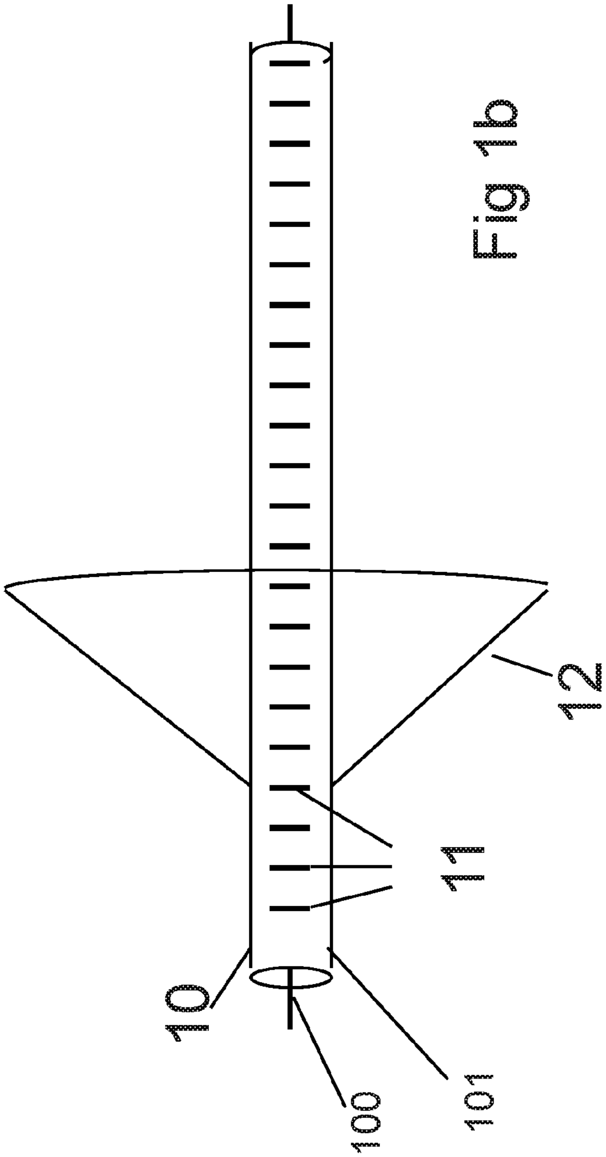

When the elongated structure is straight the symmetry dictates that the radiation pattern E(r') will be circularly symmetric around the longitudinal axis of the elongated structure. To illustrate, consider a design in which the slots are uniformly separated with a spacing of half a wavelength, and where they are excited with equal amplitude and a linear phase gradient according to $a_n = a \cdot e^{\pi i n \sin\theta}$. The radiation maximum for this design will occur in a cone with polar angle θ from the longitudinal axis. As previously mentioned with reference to FIG. 1*a*, the cable 10 operates in the coupling mode when the radiation 12 has its maximum along the cable, and the cable operates in the radiation mode when the radiation 12 has its maximum more perpendicular to the cable illustrated in FIG. 1*b*.

The radiation slots are preferably elongated slots 11 which are through-going perforations and have a main direction of extension which makes the slots radiate. The main direction of extension which makes a slot radiate differs between different kinds of cables: in a coaxial cable the main direction of extension should not coincide with the cable's main length of extension. In a waveguide, or a micro strip or strip line structure, the main direction of extension of a slot can coincide with that of the structure or cable and still radiate. It should be mentioned that, the shape of the radiation elements can be chosen from a wide variety of different kinds of perforations in the outer conductor 101 of the structure e.g. elongated rectangular or oval slots. It should however be pointed out that most shapes of perforations will give rise to a radiating effect. Also, with reference to other kinds of possible structures for guiding an electromagnetic wave, such as waveguides or strip line and micro strip structures, it can be pointed out that the perforations which form the radiation elements should be made in the conductor of such structures.

FIG. 2*a* shows a leaky cable 20 i.e. an elongated structure for guiding an electromagnetic wave which could be a coaxial cable, a waveguide, a strip line arrangement or a micro strip arrangement. The substantially straight leaky cable 20 includes radiation elements (not shown), such as the slots previously described. The leaky cable 20 exhibits a longitudinal direction of extension L in parallel with the z-axis. A projection of the radiation pattern of the leaky cable 20 in an x-y-plane in the far field is shown schematically in FIG. 2*b*. A concept of the embodiments described hereinafter is to provide a radiation pattern by superpositioning the radiation pattern of subsections of an elongated structure comprising radiation elements. A subsection exhibits a longitudinal direction of extension and a radiation pattern. Each subsection radiates with a high directivity in a cone. A predetermined radiation pattern, synthesized from the superposition of the radiation cones from each subsection, can be shaped by using different orientation of the subsections. Thus, by utilizing subsections with different orientations it is possible to create a resulting radiation pattern that has many more degrees of freedom than a prior art point source antenna or a straight leaky cable.

In FIG. 3*a* an exemplary embodiment of an antenna arrangement 30 is illustrated. An elongated structure 31 for guiding an electromagnetic wave is shown. The elongated structure 31 may be a coaxial cable, a waveguide, a strip line arrangement or a micro strip arrangement. The elongated structure 31 comprises subsections 32, 33, 34 and radiation elements 35. It should be pointed out that a structure could comprise several subsections however only three are illustrated in FIG. 3. The radiation elements 35 are through-going perforations, such as the slots previously described, in the elongated structure. Each perforation 35 is adapted to allow a fraction of the total energy in the guided electromagnetic wave to be radiated out from the perforation. Furthermore, each subsection 32, 33, 34 exhibits a longitudinal direction of extension $L_{32}$, $L_{33}$, $L_{34}$. The longitudinal directions of extension $L_{32}$, $L_{33}$, $L_{34}$ are inclined to the z-axis. Furthermore, each subsection 32, 33, 34 exhibits a radiation pattern 36, 37, 38. In an embodiment wherein the longitudinal directions of adjacent subsections $L_{32}$, $L_{33}$, $L_{34}$ are oriented in different directions, a predetermined radiation pattern by superpositioning of the radiation pattern of each subsection 36, 37, 38 is created. A projection of the predetermined radiation pattern of the antenna arrangement 30 in the x-y-plane in the far field is shown schematically in FIG. 3*b*.

The predetermined radiation pattern can be given more complex shapes than the shape of a cone. As is indicated in FIG. 3*b* an antenna arrangement comprising subsections creates a radiation pattern providing a more elongated coverage zone than the antenna arrangement comprising a straight elongated structure.

The predetermined radiation pattern can be given more complex shapes by orienting the different directions of adjacent subsections in such a way that they differ by substantially the same angle. However, in another embodiment the may differ by different angles. Moreover, the adjacent subsections may exhibit substantially the same lengths or different lengths.

In exemplary embodiments a more elaborate radiation element structure may be provided. The slot separation in a subsection may be substantially equal or non-equal. The slot separation may also vary amongst the different subsections. Additionally, the subsections may radiate with substantially the same characteristics such as power or cone angle. However, the subsections may also be made to radiate with different characteristics. By changing the shape, separation and characteristics of the subsections a desired predetermined radiation pattern could be created. Thus, a more uniform coverage within the intended coverage area can be achieved.

Figure 4A:
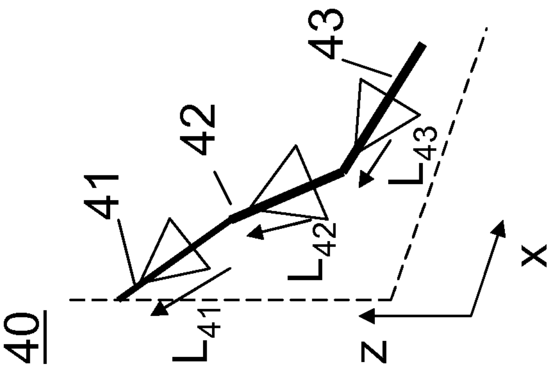
FIG. 4*a* shows an antenna arrangement according to another exemplary embodiment and the projection of the corresponding radiation pattern in the x-y-plane is illustrated in FIG. 4*b*.
Figure 4B:
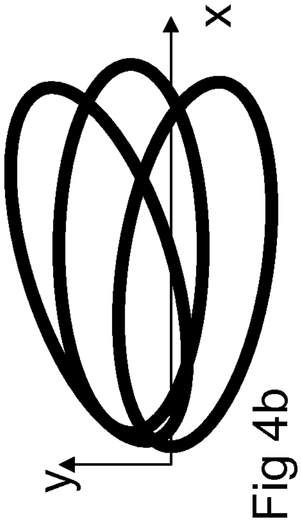
Figure 5A:
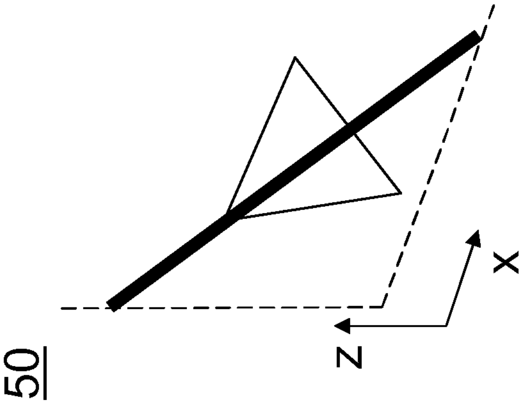
FIG. 5*a* shows a substantially straight leaky cable and the projection of the corresponding radiation pattern in the x-y-plane is illustrated in FIG. 5*b*.
Figure 5B:
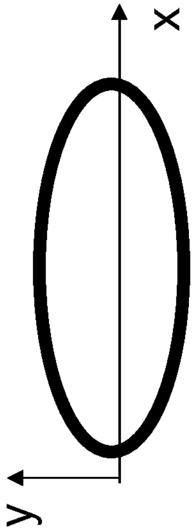

In FIG. 4*a* yet another exemplary embodiment of an antenna arrangement 40 comprising subsections 41, 42, 43 is illustrated. The longitudinal directions of extension of the subsections $L_{41}$, $L_{42}$, $L_{43}$ are inclined to the x-z-plane. Such an orientation may be preferable in practical deployments, for instance when the antenna arrangement should be mounted on a sloping building roof. For a straight antenna arrangement 50, as shown in FIG. 5*a*, it is difficult to achieve e.g. uniform sector coverage as the intersection of the conical radiation pattern with the x-y-plane, i.e. the ground, will be shaped as an ellipse as illustrated in FIG. 5*b*. However, if the leaky cable is partitioned into subsections, e.g. three subsections, with different orientations of the longitudinal directions $L_{41}$, $L_{42}$, $L_{43}$ then the projection from each subsection will trace out an ellipse with a different orientation as shown in FIG. 4*b*. Hence, the superposition of the radiation patterns from the subsections can as a result become more suitable for sectorized cell coverage. Additionally, as mentioned previously by changing the shape, separation and characteristics of the subsections a desired predetermined radiation pattern could be created and the coverage inside the elliptical area can be "filled in". Thus, a more uniform coverage within the intended coverage area can be achieved.

Figure 6:
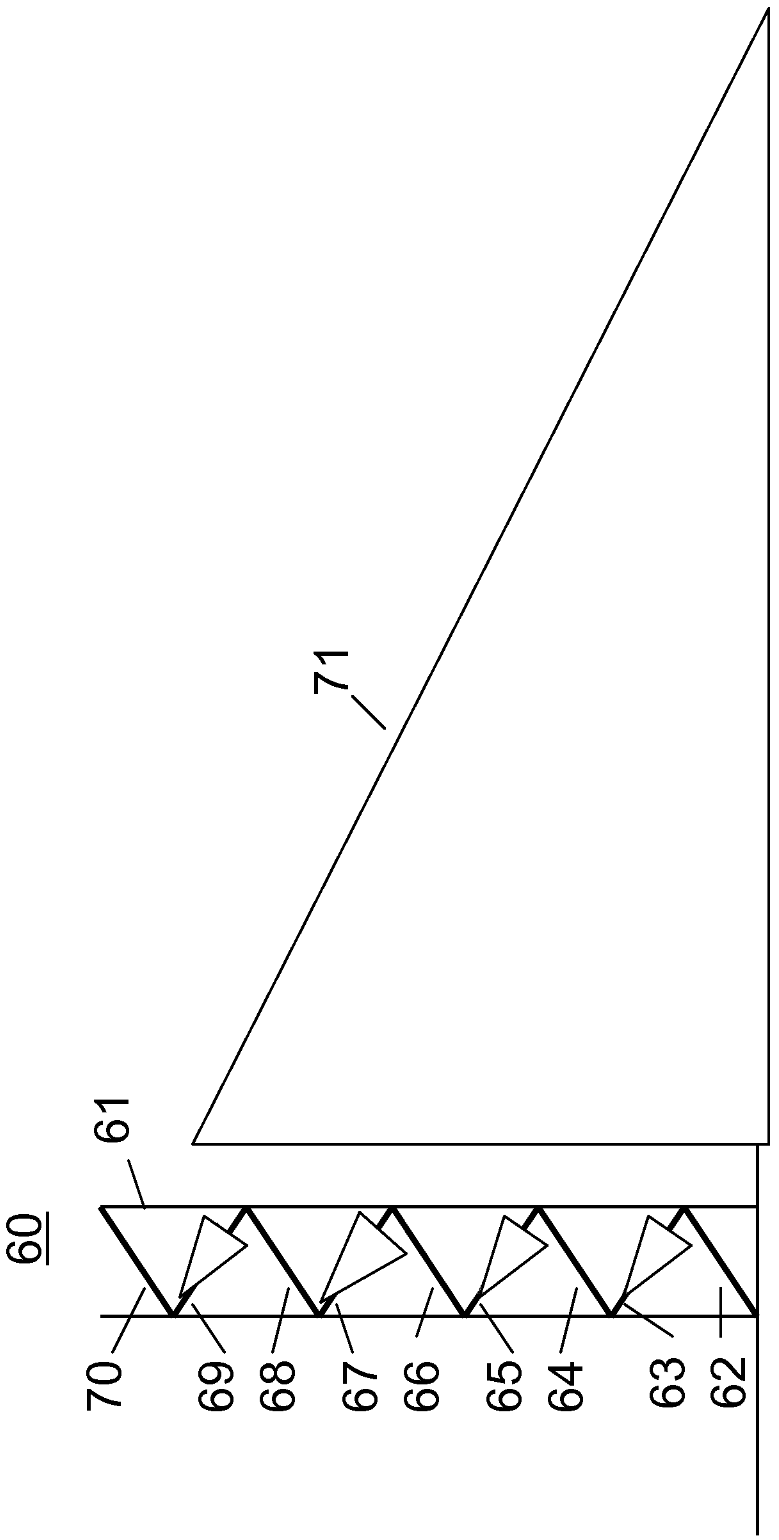
FIG. 6 shows an antenna arrangement and the projection of the corresponding radiation pattern according to yet another exemplary embodiment.

Yet another exemplary embodiment is illustrated in FIG. 6, wherein the antenna arrangement 60 is adapted to be attached to a truss structure 61 that is commonly used in free-standing towers and to be used by a radio base station in a wireless communication system. In this example the antenna arrangement 60 is further modified in order to only radiate from some subsections 63, 65, 67, 69 of the plurality of subsections 62-70. By letting subsections not adjacent to each other and having the same orientation of the longitudinal directions of extension radiate a directed predetermined radiation pattern 71 is created. By additionally changing the shape, separation and characteristics of the subsections a different directed predetermined radiation pattern may be created.

It should be pointed out that the antenna arrangement could be mounted on any constructed or any natural structure. Examples of such structures are: a tower, mast, building wall, tree, flag pole or cliff etc.

A further exemplary embodiment relates to the use of an antenna arrangement in small devices such as hand-held telephones or computer devices. The use of the antenna arrangement previously described results in a more uniform excitation of currents over the chassis of the device, which in turn results in both a more uniform radiation pattern as well as lower losses due to detuning or absorption.

Figure 7:
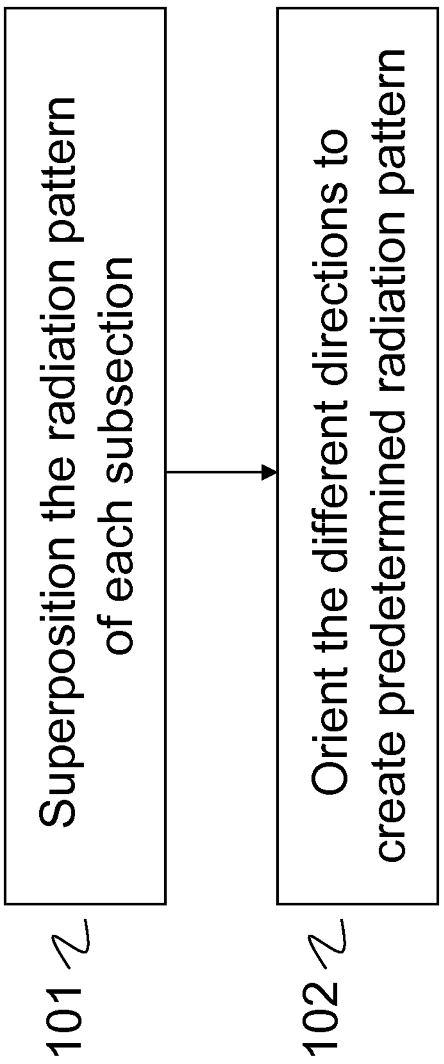
FIG. 7 is a flow diagram illustrating a method for creating a predetermined radiation pattern of an antenna arrangement according to an embodiment of the present invention.

FIG. 7 is a flow diagram illustrating a method for creating a predetermined radiation pattern of the antenna arrangement according to previously described exemplary embodiments. The antenna arrangement comprises an elongated structure for guiding an electromagnetic wave and the structure comprises subsections and radiation elements. The radiation elements are through-going perforations in the elongated structure and each perforation is adapted to allow a fraction of the total energy in the guided electromagnetic wave to be radiated out from the perforation. Each subsection exhibits a longitudinal direction of extension and a radiation pattern. The method comprises the step of superpositioning 101 the radiation pattern of each subsection. Furthermore, the method includes orienting 102 said longitudinal directions of adjacent subsections in different directions to create said predetermined radiation pattern.

The present invention may, of course, be carried out in other ways than those specifically set forth herein without departing from essential characteristics of the invention. The present embodiments are to be considered in all respects as illustrative and not restrictive.

The invention claimed is:

1. An antenna arrangement comprising an elongated structure for guiding an electromagnetic wave, said elongated structure comprising:

- a first subsection comprising first radiation elements;
- a second subsection;
- a third subsection comprising second radiation elements, wherein
- said first, second and third subsections are serially connected,
- said radiation elements are through-going perforations in the elongated structure, each said perforation adapted to allow a fraction of the total energy in the guided electromagnetic wave to be radiated out from the perforation,
- the first, second and third subsections each exhibiting a longitudinal direction of extension,
- the first subsection exhibiting a first radiation pattern and the third subsection exhibiting a second radiation pattern,
- said longitudinal directions of adjacent serially connected subsections are oriented in different directions to create a predetermined radiation pattern by superpositioning of the first and second radiation patterns,
- an angle between said longitudinal directions of adjacent serially connected subsections is formed and said angle between said longitudinal directions of adjacent serially connected subsections is substantially greater than 90 degrees and less than 180 degrees,
- each of said subsections comprises an inner conductor and an outer conductor for shielding the inner conductor, and
- the second subsection does not have any through-going perforations.

2. The antenna arrangement according to claim 1, wherein said different directions of adjacent subsections are oriented to differ by substantially the same angle.

3. The antenna arrangement according to claim 1, wherein the adjacent subsections exhibit substantially the same lengths.

4. The antenna arrangement according to claim 1, wherein the adjacent subsections exhibit different lengths.

5. The antenna arrangement according to claim 1, wherein the adjacent subsections comprise radiation elements of substantially the same shape.

6. The antenna arrangement according to claim 1, wherein the adjacent subsections comprise radiation elements of different shapes.

7. The antenna arrangement according to claim 1, wherein the adjacent subsections comprise radiation elements with a substantially equal slot separation.

8. The antenna arrangement according to claim 1, wherein the adjacent subsections comprise radiation elements with a non-equal slot separation.

9. The antenna arrangement according to claim 1, wherein the adjacent subsections radiate with the substantially same characteristics such as power or cone angle.

10. The antenna arrangement according to claim 1, wherein the adjacent subsections radiate with different characteristics such as power or cone angle.

11. The antenna arrangement according to claim 1, wherein the elongated structure is one of the following: a coaxial cable, a waveguide, a strip line arrangement and a micro strip arrangement.

12. The antenna arrangement according to claim 1, adapted to be used by a radio base station or in a user equipment.

13. The antenna arrangement according to claim 12, wherein the user equipment is a hand-held telephone or a computer device.

14. A method of creating a predetermined radiation pattern of an antenna arrangement, wherein said antenna arrangement comprises an elongated structure for guiding an electromagnetic wave, said structure comprising a first subsection having first radiation elements, a second subsection, and a third subsection having second radiation elements, wherein said subsections are serially connected and said radiation elements are through-going perforations in the elongated structure, each said perforation adapted to allow a fraction of the total energy in the guided electromagnetic wave to be radiated out from the perforation, each subsection exhibiting a longitudinal direction of extension, the first subsection exhibiting a first radiation pattern, and the third subsection exhibiting a second radiation pattern, the method comprising:

- superpositioning the radiation patterns of the first and third subsections; and
- orienting said longitudinal directions of adjacent serially connected subsections in different directions to create said predetermined radiation pattern and to create an angle between said longitudinal directions of adjacent serially connected subsections, wherein said angle between said longitudinal directions of adjacent serially connected subsections is substantially greater than 90 degrees and less than 180 degrees, wherein
- each of said subsections comprises an inner conductor and an outer conductor for shielding the inner conductor, and
- the second subsection does not have any through-going perforations.

15. The method according to claim 14, wherein said orienting is performed by orienting said different directions of adjacent subsections to differ by substantially the same angle.

16. The method according to claim 14, wherein the adjacent subsections exhibit substantially the same lengths.

17. The method according to claim 14, wherein the adjacent subsections exhibit different lengths.

18. The method according to claim 14, wherein the adjacent subsections comprise radiation elements of substantially the same shape.

19. The method according to claim 14, wherein the adjacent subsections comprise radiation elements of different shapes.

20. The method according to claim 14, wherein the adjacent subsections comprise radiation elements with a substantially equal slot separation.

21. The method according to claim 14, wherein the adjacent subsections comprise radiation elements with a non-equal slot separation.

22. The method according to claim 14, wherein the adjacent subsections radiate with the substantially same characteristics such as power or cone angle.

23. The method according to claim 14, wherein the adjacent subsections radiate with different characteristics such as power or cone angle.

24. The method according to claim 14, wherein the elongated structure is one of the following: a coaxial cable, a waveguide, a strip line arrangement and a micro strip arrangement.

25. The method according to claim 14, is used in a radio base station or in a user equipment.

26. The method according to claim 25, wherein the user equipment is a hand-held telephone or a computer device.

27. A leaky antenna arrangement, comprising:

a first elongated structure for guiding an electromagnetic wave;

a second elongated structure for guiding an electromagnetic wave; and a third elongated structure for guiding an electromagnetic wave, said second elongated structure having a first end connected to a first end of the first elongated structure and having a second end connected to a first end of the third elongated structure, wherein the first elongated structure extends along a first straight line, the second elongated structure extends along a second straight line, the third elongated structure extends along a third straight line, said straight lines are co-planar, said first line intersects said second line at a point, thereby forming an angle between the first line and the second line, said second line intersects said third line at a point, thereby forming an angle between the second line and third line, said angle between the first line and the second line being substantially greater than or less than 90 degrees and being less than 180 degrees, said angle between the second line and third line being substantially greater than or less than 90 degrees and being less than 180 degrees, said first elongated structure comprises a first inner conductor and a first outer conductor and a first set of apertures formed in the first outer conductor for causing the first elongated structure to function as a leaky cable antenna, and said third elongated structure comprises a second inner conductor and a second outer conductor and a second set of apertures formed in the second outer conductor for causing the third elongated structure to function as a leaky cable antenna, wherein said first elongated structure has a first main direction of extension, each aperture included in the first set of apertures has a main direction of extension that does not coincide with said first main direction of extension, said third elongated structure has a second main direction of extension, and each aperture included in the second set of apertures has a main direction of extension that does not coincide with said second main direction of extension, wherein the second elongated structure does not have any apertures, said angle between the first line and the second line is substantially greater than 90 degrees and less than 180 degrees, and said angle between the second line and third line is substantially greater than 90 degrees and less than 180 degrees.

* * * * *